United States Patent
Jiang et al.

(10) Patent No.: US 11,969,717 B2
(45) Date of Patent: Apr. 30, 2024

(54) ORGANOPHOSPHORUS DEGRADING ENZYME BASED MULTIFUNCTIONAL CATALYST AND PREPARATION METHOD AND USE THEREOF

(71) Applicant: Hebei University of Technology, Tianjin (CN)

(72) Inventors: Yanjun Jiang, Tianjin (CN); Liya Zhou, Tianjin (CN); Saiguang Xue, Tianjin (CN); Jing Gao, Tianjin (CN)

(73) Assignee: Hebei University of Technology, Tianjin (CN)

( * ) Notice: Subject to any disclaimer, the term of this patent is extended or adjusted under 35 U.S.C. 154(b) by 244 days.

(21) Appl. No.: 17/317,470

(22) Filed: May 11, 2021

(65) Prior Publication Data
US 2021/0346876 A1 Nov. 11, 2021

(30) Foreign Application Priority Data
May 11, 2020 (CN) .......................... 202010391650.9

(51) Int. Cl.
| | |
|---|---|
| C12N 9/16 | (2006.01) |
| B01J 21/08 | (2006.01) |
| B01J 21/18 | (2006.01) |
| B01J 23/75 | (2006.01) |
| B01J 23/755 | (2006.01) |
| B01J 31/00 | (2006.01) |
| B01J 35/00 | (2006.01) |
| B01J 37/00 | (2006.01) |
| B01J 37/04 | (2006.01) |
| C07C 209/32 | (2006.01) |
| C07C 201/06 | (2006.01) |
| C07C 205/22 | (2006.01) |

(52) U.S. Cl.
CPC ............. *B01J 31/003* (2013.01); *B01J 21/08* (2013.01); *B01J 21/18* (2013.01); *B01J 23/75* (2013.01); *B01J 23/755* (2013.01); *B01J 35/008* (2013.01); *B01J 35/0086* (2013.01); *B01J 37/009* (2013.01); *B01J 37/04* (2013.01); *C07C 209/325* (2013.01); *C12N 9/16* (2013.01); *C07C 201/06* (2013.01); *C07C 205/22* (2013.01); *C07K 2319/21* (2013.01)

(58) Field of Classification Search
CPC ..................................... C12N 9/16; A62D 3/02
See application file for complete search history.

(56) References Cited

PUBLICATIONS

Li-Sen Lin et al., Adv. Mater. 2018, 30, 1704639, Yolk Shell Nanostructures Design Synthesis and Biomedical Applications (Year: 2018).*

* cited by examiner

*Primary Examiner* — Tekchand Saidha
(74) *Attorney, Agent, or Firm* — Morse, Barnes-Brown & Pendleton, P.C.; Martin Z. Zhang, Esq.

(57) ABSTRACT

The present disclosure provides a method for preparing an organophosphorus degrading enzyme based multifunctional catalyst and an organophosphorus degrading enzyme based multifunctional catalyst and use thereof. In the present disclosure, the preparation method includes: directly adding a composite yolk-shell-structured nanomaterial into a crude enzyme solution of organophosphorus degrading enzyme with an affinity tag, and mixing, to obtain a mixture, and then subjecting the mixture to a separation, to obtain an organophosphorus degrading enzyme based multifunctional catalyst. According to the present disclosure, the method for preparing an organophosphorus degrading enzyme based multifunctional catalyst is simple in operation, and has a low cost; the multifunctional catalyst prepared by the same has low requirement for the purity of enzyme, support of which could be directionally binded with enzyme, and could be used for detecting an organophosphorus pesticide, and also for a cascade degradation of an organophosphorus pesticide. The final product p-aminophenol has important application value.

4 Claims, 1 Drawing Sheet

ORGANOPHOSPHORUS DEGRADING ENZYME BASED MULTIFUNCTIONAL CATALYST AND PREPARATION METHOD AND USE THEREOF

CROSS REFERENCE TO RELATED APPLICATIONS

The present application claims priority to Chinese Patent Application No. 202010391650.9, filed on May 11, 2020. The content thereof is hereby incorporated by reference in its entirety.

TECHNICAL FIELD

The present disclosure relates to the technical field of the preparation of biocatalyst, and in particular to a method for preparing an organophosphorus degrading enzyme based multifunctional catalyst. Furthermore, the present disclosure relates to the organophosphorus degrading enzyme based multifunctional catalyst prepared by the method and use of the same in the detection and degradation of an organophosphorus pesticide.

BACKGROUND

Organophosphorus pesticide is a pesticide widely used in agriculture insecticide, and it comprises a large amount of organophosphorus compound. However, the organophosphorus compound is one of currently known substances that has a high toxicity. A wide use of the organophosphorus pesticide has caused great pollution to the environment, and serious hazard to human health; thus, the detection and degradation thereof is very important.

In recent years, great progress has been made in the research of biodegradation of organophosphorus pesticide by using biotechnology. Compared with the potential drawbacks of traditional methods, biological methods have been more attractive. The biological method has a less destruction and a lower cost. The catalyst used, however, exhibits poor stability, and thus could not be recycled; the purification steps are complex, and the degradation is incomplete, which limits the applications of the biological method.

It is well known that the immobilization of enzyme is an effective method to solve the problems of the instability and non-recyclability of enzyme catalyst, but all traditional immobilization methods need a purification step of enzyme prior to the immobilization of enzyme. In order to solve the complex enzyme purification step, the enzyme genes and the histidine affinity tag genes are always recombined and then purified. Thus, in recent years, people pay more and more attention to the protein separation and purification system based on nanoparticles functionalized by immobilized metal affinity chromatography (IMAC). However, the steps of such method are still tedious, and in the use of chelating agent, when the metal ions of metal enzyme active center may interact with chelating agent, the metal enzyme activity would be negatively affected (such as organophosphate degrading enzyme).

SUMMARY

In view of this, the present disclosure is to provide a method for preparing an organophosphorus degrading enzyme based multifunctional catalyst, and the organophosphorus degrading enzyme based multifunctional catalyst prepared by the same could overcome the problems of the existing organophosphorus degrading enzyme: poor stability and incomplete degradation in terms of the final product when used to degrade the organophosphorus pesticide.

In order to achieve the above object, the technical solutions of the present disclosure are provided as follows:

A method for preparing an organophosphorus degrading enzyme based multifunctional catalyst, comprising,
directly adding a composite yolk-shell-structured nanomaterial into a crude enzyme solution of an organophosphorus degrading enzyme with an affinity tag, and mixing, to obtain a mixture, and subjecting the mixture to a separation, to obtain the organophosphorus degrading enzyme based multifunctional catalyst.

In some embodiments, the composite yolk-shell-structured nanomaterial is $Co/C@SiO_2@Ni/C$.

In some embodiments, the affinity tag is selected from the group consisting of histidine tag, cysteine tag, and tryptophan tag.

In some embodiments, the organophosphorus degrading enzyme is coded by a gene sequence obtained from soil *pseudomonas, flavobacterium*, or *agrobacterium* radioactive.

In some embodiments, the mixing is performed by using a shaking table or stirring for 0.5-6 hours; subjecting the mixture to a separation is performed by a centrifugation or filtration.

Compared with the prior art, the present disclosure has the following beneficial effects:

In the method for preparing an organophosphorus degrading enzyme based multifunctional catalyst according to the present disclosure, the composite yolk-shell-structured nanomaterial which is rich in transition metal ions in itself is used to further purify and immobilize the organophosphorus degrading enzyme with an affinity tag, and it would effectively solve the drawbacks of the poor stability, inability to recycle, and complex purification during the enzyme catalysis. The method as described above is simple in operation, has a lower requirement for the purity of enzyme, thus there is no need to carry out costly separation and purification of enzyme, and the support could be directionally binded with enzyme. The prepared organophosphorus degrading enzyme based multifunctional catalyst could be used for detecting the organophosphorus pesticide, and also for a cascade degradation of the organophosphorus pesticide.

Furthermore, the present disclosure provides an organophosphorus degrading enzyme based multifunctional catalyst prepared by the method for preparing an organophosphorus degrading enzyme based multifunctional catalyst as described above.

In addition, the present disclosure also provides use of the organophosphorus degrading enzyme based multifunctional catalyst for detecting or degrading an organophosphorus pesticide.

In some embodiments, detecting the organophosphorus pesticide is performed by an optical detection method.

In some embodiments, the organophosphorus degrading enzyme based multifunctional catalyst is used in accompany with a hydrogen donor to degrade the organophosphorus pesticide.

In some embodiments, the hydrogen donor is sodium borohydride.

The organophosphorus degrading enzyme based multifunctional catalyst could be used for detecting or degrading an organophosphorus pesticide. The final product obtained after the degradation is non-toxic, and have a wide range of applications and good application effects.

BRIEF DESCRIPTION OF THE DRAWINGS

The accompanying drawings which constitute part of the present disclosure are used to provide a further understanding of the present disclosure. The schematic embodiments of the present disclosure and the illustrations thereof are used to explain the present disclosure, and do not constitute an undue limitation of the present disclosure. In the accompanying drawings.

DETAILED DESCRIPTION OF THE EMBODIMENTS

Figure 1:
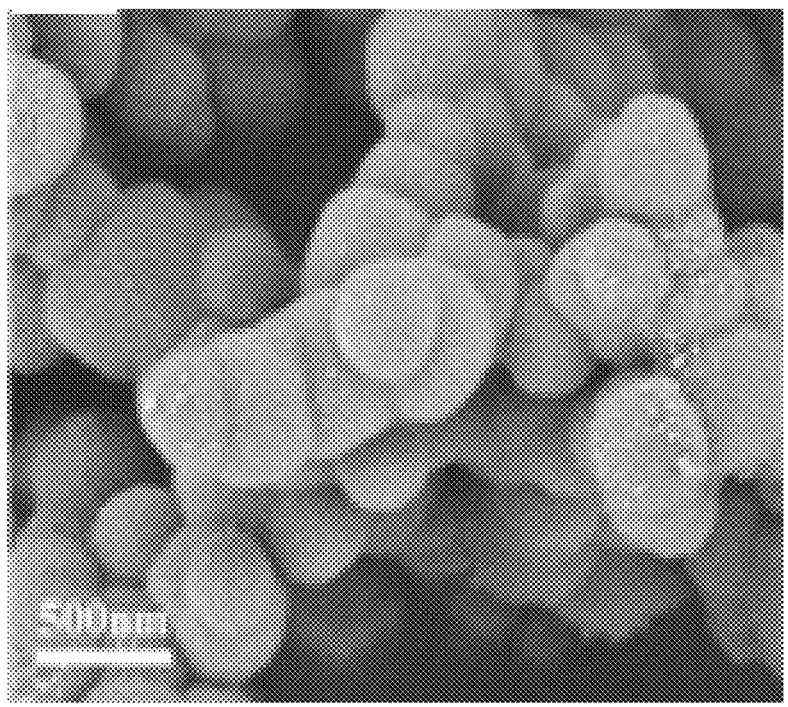
FIG. 1 shows a scanning electron micrograph of Co/C@SiO$_2$@Ni/C of Example 1 of the present disclosure.

It is noted that the embodiments in the present disclosure and the characteristics in the embodiments may be combined with each other if not conflict. At the same time, the specific conditions not specified in the present disclosure, may be conventional conditions or those recommend by the manufacturers of equipments used. The reagents or instruments used that are not specified in manufacturers, may be conventional and commercially available products. For the technical means or techniques involved, if the conditions are not specified, it may mean that the existing means in the field thereof could be used.

The present disclosure will be further described in detail below in conjunction with embodiments and accompanying drawings.

This embodiment involves a method for preparing an organophosphorus degrading enzyme based multifunctional catalyst, and in the method, a composite yolk-shell-structured nanomaterial is used as a support, and an organophosphorus degrading enzyme with an affinity tag is used as a target enzyme. The support is directly added into a crude enzyme solution of a target enzyme, and they are adequately mixed for reacting, to obtain a mixture, and the mixture is subjected to a separation, to obtain the organophosphorus degrading enzyme based multifunctional catalyst.

In this embodiment, the composite yolk-shell-structured nanomaterial is a mesoporous material with a clear core-shell structure, which is formed from a self-assembly of an organic ligand containing oxygen and nitrogen (mostly aromatic polyacids and polybases) and a transition metal ion, after being covered with silica, coated with dopamine and a transition metal ion, and then being calcined. The composite yolk-shell-structured nanomaterial has the advantages of low density, large surface area, good chemical and mechanical stability, and high permeability for charge and molecule transport. According to the present disclosure, the composite yolk-shell-structured nanomaterial is used as a support to prepare the organophosphorus degrading enzyme based multifunctional catalyst.

The affinity tag is a sequence of amino acid that has a high affinity for a particular biological or chemical ligand. The fusion of the affinity tag with a protein is not only convenient for the detection and purification of the fused protein, but also affects the physical and chemical properties of the target protein. The fusion, however, is generally required not to produce influences, otherwise which would negatively affect the activity of the enzyme. According to the present disclosure, the organophosphate degrading enzyme with an affinity tag is selectively binded with the support, through the interaction between the transition metal ions (Cu$^{2+}$, Ni$^{2+}$, Co$^{2+}$, Zn$^{2+}$, etc.) on the support of the composite yolk-shell-structured nanomaterial with existing amino acid residues (e.g., imidazolyl, sulfydryl and indolyl group(s) of histidine, cysteine and tryptophan).

The organophosphate degrading enzyme is a kind of protein that can catalyze P—O bond, P—F bond and P—S bond in the organophosphorus substance to crack, and is featured by high catalytic efficiency and a wide range of substrate when used for the degradation of the organophosphorus pesticide, and thus could be used to catalyze the degradation of many kinds of organic phosphorus compound (such as parathion-methyl, paraoxon, parathion, coumaphos, diazinon and isoflurophate). Thus, in order to protect the environment and human health, reducing the residues of the organophosphorus compound in nature, degrading the organophosphorus compound by using organophosphorus degrading enzyme has a great prospect. According to the present disclosure, the organophosphorus degrading enzyme is selected to bind with the support to prepare an immobilized enzyme, which is used for the degradation of the organophosphorus compound in the environment.

Although the organophosphorus degrading enzymes could be used to degrade the organophosphorus compound, only degrading them into p-nitrophenol. Although the toxicity of p-nitrophenol is many times lower than that of the organophosphorus compound, it is still a toxic substance that could cause environmental pollution, thus, it could not completely solve the pollution problem of the organophosphorus compound to the environment. In order to better restore the ecosystem damaged by the organophosphorus pesticide, on the basis of the organophosphorus degrading enzyme, the immobilization thereof is achieved by using the composite yolk-shell-structured nanomaterial, and the obtained catalyst is used to catalyze the further degradation of p-nitrophenol to generate p-aminophenol, in the presence of a hydrogen donor. Moreover, p-aminophenol is an important pharmaceutical intermediate, and thus the catalyst could not only enable the complete degradation of organophosphorus compound, but also provide a wide range of application value.

Crude enzyme solution refers to a mixed solution containing the target enzyme obtained by removing macromolecular substances, such as cell walls or organelles, from a microorganism, after microbial fermentation. The existing process for preparing of a biocatalyst has a high requirement for the purity of the target enzyme, and thus it is needed to subject the crude enzyme solution obtained after microbial fermentation to complex separation and purification process (es), which leads to a high cost. According to the present disclosure, directly combining the support with the crude enzyme solution could omit the separation and purification step of the crude enzyme solution, thereby greatly reducing the production cost.

According to the present disclosure, in the method, a composite yolk-shell-structured nanomaterial is used as a support, and an organophosphorus degrading enzyme with an affinity tag is used as a target enzyme. The support is directly added into a crude enzyme solution containing the target enzyme, and they are adequately mixed for reacting, to obtain a mixture, and the mixture is subjected to a separation, to obtain the organophosphorus degrading enzyme based multifunctional catalyst.

As the organic ligand and metal ions in the composite yolk-shell-structured nanomaterial could be selected, thus different types of yolk-shell-structured nanomaterial could be synthesized by combining different types of organic ligands and different transition metal elements.

According to the present disclosure, the material with better performance could be selected as the support by limiting the type of the composite yolk-shell-structured nanomaterial, in order to make the prepared organophosphorus degrading enzyme based multifunctional catalyst exhibit higher enzyme utilization rate, and better enzyme activity. By further selecting the yolk-shell-structured nanomaterial, the organophosphorus degrading enzyme utilization rate and the enzyme activity of the organophosphorus degrading enzyme based multifunctional catalyst could be further increased.

In some embodiments, a preferred composite yolk-shell-structured nanomaterial is generally prepared by a method comprising the following steps:

A 2-methyl imidazole solution and a $Co(NO_3)_2 \cdot 6H_2O$ solution are mixed, fully shook and sonicated for 10 min, stirred at room temperature for 6 h, and the resulting mixture is subjected to a separation by a centrifugation, to obtain a precipitate. The precipitate (i.e. ZIF67) is washed in sequence with ultrapure water and ethanol 3 times each, and the washed precipitate was ultrasonically dispersed into anhydrous ethanol. The 2-methyl imidazole solution is added therein, and they are fully shook and sonicated for 5 min to be uniform. Then a cetyltrimethylammonium chloride (5 wt %) solution is added therein, and they are stirred for 5 min at room temperature. Then, ethyl orthosilicate (TEOS) is slowly added dropwise into the mixed solution above and they are stirred at room temperature for 1.5 h. The resulting mixture is subjected to a separation by a centrifugation, to obtain a precipitate. The precipitate (ZIF67@SiO$_2$) is washed with ultrapure water 3 times and washed with ethanol 3 times. The washed precipitate is ultrasonically dispersed in ethanol solution again and mixed with Tris solution, to obtain a mixed solution. Then dopamine and $NiCl_2 \cdot 6H_2O$ are added into the mixed solution in sequence, and after dopamine and $NiCl_2 \cdot 6H_2O$ being dissolved completely, the resulting mixture are stirred at room temperature for 15 h. The mixture obtained after stirring is subjected to a separation by a centrifugation (9000 rpm, 5 min), to obtain a precipitate. The precipitate is washed with ultrapure water and ethanol several times, and the washed precipitate is dried, to obtain a precursor material. The precursor material is placed in a quartz crucible and calcined at 500° C. for 2 h, with a heating rate of $2°\text{ C.} \cdot \text{min}^{-1}$, under the protection of nitrogen, to obtain the composite yolk-shell-structured nanomaterial Co/C@SiO$_2$@Ni/C.

In some embodiments, a preferred organophosphorus degrading enzyme based multifunctional catalyst is generally prepared by a method comprising the following steps.

The composite yolk-shell-structured nanomaterial is added into the Tris-HCl buffer solution, and they are sonicated for 2 mM to be uniformly dispersed, and the uniformly dispersed composite yolk-shell-structured nanomaterial is added into a crude enzyme solution, and they are evenly mixed, shook on a shaking table at room temperature for 3 h. The resulting mixture is subjected to a centrifugation, to obtain a precipitate. The precipitate is washed with imidazole buffer solution (40 mM) three times, to obtain a washed precipitate, i.e. the organophosphorus degrading enzyme based multifunctional catalyst OpdA@Co/Ad@Ni/C.

In some embodiments, the affinity tag includes histidine tag (His-Tag), cysteine tag (Cys Tag) and tryptophan tag (Trp-Tag), and is preferably histidine tag, mainly because histidine tag has a small molecular weight and generally does not affect the target protein. By further selecting the type of the affinity tag, the target enzyme with an affinity tag could be binded with the support more firmly, so as to improve the enzyme utilization rate and the enzyme activity of the organophosphorus degrading enzyme based multifunctional catalyst. However, in addition to the affinity tags described above, other affinity tags that could be binded with transition metal ions known to those skilled in the art may be used.

In some embodiments, the gene sequence that codes the organophosphorus degrading enzyme in the organophosphorus degrading enzyme with an affinity tag is obtained from *pseudomonas agrobacterium, flavobacterium*, or radioactive *agrobacterium*, and preferably is obtained from the gene sequence that codes organophosphorus degrading enzyme in radioactive *agrobacterium*. By the existing genetic engineering method, the affinity tags is introduced into the N-terminal of the gene that codes organophosphorus degrading enzyme, to obtain the desired gene sequence. Then the desired gene sequence is transformed in a transforming plasmid and expressed in a expressing bacteria, to obtain the organophosphorus degrading enzyme with an affinity tags. There are types of organophosphorus degrading enzyme, and different types of organophosphorus degrading enzymes exhibit different catalytic efficiency and could be applied to different substrate ranges. In the present disclosure, the organophosphorus degrading enzyme used is the organophosphorus degrading enzyme of *pseudomonas agrobacterium, flavobacterium*, or radioactive *agrobacterium*, thereby enabling the catalyst to exhibit a higher catalytic efficiency, and to be applied to a wider substrate range.

*Pseudomonas agrobacterium, flavobacterium* and radioactive *agrobacterium* in the present disclosure are commercially available, or obtained by a isolation in the laboratory, and the gene sequences that code the organophosphate degrading enzyme of the above three kinds of bacteria could be found from the website (https://www.ncbi.nlm.nih.gov/, among which, *pseudomonas agrobacterium* is named OPD, GenBank: AER10490.1; *flavobacterium* is named OPD, GenBank: AAV39527.1; radioactive *agrobacterium* is named OPDA, GenBank: AAK85308.1). An affinity tag is introduced into a gene sequence that codes the organophosphorus degrading enzyme, which is obtained from one of the above three bacteria, to obtain a desired gene sequence; the desired gene sequence is transformed in a plasmid; the plasmid is transferred into an expressing bacteria, i.e., the host bacteria (e.g. *Escherichia coli*) for expression, and the result of the expression is to obtain a product, i.e. the organophosphorus degrading enzyme required in the present disclosure.

The recombinant strain (i.e. *Escherichia coli* above) which can express the affinity tag is subjected to a fermentation first, after the fermentation, the cells in the fermentation broth are lyzed, then centrifuged, to obtain the desired crude enzyme solution of organophosphorus degrading enzyme with an affinity tag.

According to the present disclosure, after adding the support into the crude enzyme solution, a mixing is needed to achieve a full binding of the support and the target enzyme. The mixing may be performed by using a shaking table or stirring, preferably by using a shaking table, or by using other means for mixing known to those skilled in the art. For using the shaking table or stirring, in general, the means for mixing could be selected according to the performance of the support. For example, for the support with smaller structural strength, the mixing preferably is performed by using a shaking table, to avoid the destruction of the support during the mixing, and for the support with high structural strength, the mixing preferably is performed by stirring.

The binding of the support and the target enzyme take a certain period of time, and the mixing time of the support and target enzyme could affect the binding degree of the support and the target enzyme. Generally speaking, within a certain period of time, a longer mixing time would bring a better binding of the support and the target enzyme. The mixing time in the present disclosure is specifically 0.5-6 h, and may be, for example, 0.5 h, 1 h, 2 h, 3 h, 4 h, 5 h or 6 h, preferably 3 h. Moreover, in the present disclosure, a better binding of the support and the target enzyme could be achieved by further optimizing and adjusting the mixing time, in order to improve the enzyme utilization rate.

According to the present disclosure, after mixing the support and the target enzyme to achieve a full binding, the resulting mixture is further subjected to a separation to remove fermentation broth, to obtain the organophosphorus degrading enzyme based multifunctional catalyst. The separation may be performed by a centrifugation or filtration, or other means for separation known to those skilled in the art.

The method of the present disclosure is simple in operation, and has a low requirement for the purity of enzyme, and there is no need to carry out costly separation and purification process of the enzyme. Moreover, in the method, the support could be directionally binded with the enzyme, avoiding the destruction of enzyme active site during the binding. Thus the method enables a high enzyme utilization rate, overcomes the deficiencies of low enzyme utilization rate and high purity requirement for enzyme during the existing biocatalyst preparation, and could be used to effectively degrade organophosphorus pesticide.

In addition, the present disclosure also involves the organophosphorus degrading enzyme based multifunctional catalyst prepared by the method as described above, and use thereof in the degradation of organophosphorus pesticide.

The organophosphorus degrading enzyme based multifunctional catalyst prepared in the present disclosure is low in cost and exhibits high enzyme activity, and thus it is an organophosphorus biological nanocatalyst that could be used to effectively degrade organophosphorus pesticide.

The method of the present disclosure will be further illustrated with reference to specific preparation example below.

During the preparation of the organophosphorus degrading enzyme based multifunctional catalyst, the composite yolk-shell-structured nanomaterial was used as a support, the gene sequence that codes the organophosphorus degrading enzyme with an affinity tag was obtained from radioactive *agrobacterium*, and *Escherichia coli* was used as expressing bacterium. Thereby, the organophosphorus degrading enzyme labeled with the affinity tag was prepared.

The specific preparation steps were as follows:

20 mL of 2-methyl imidazole solution (with a concentration of 0.275 g/mL) and 3 mL $Co(NO_3)_2 \cdot 6H_2O$ (with a concentration of 0.15 g/mL) solution were mixed. and sonicated for 10 min, and then stirred at room temperature for 6 h, and the resulting mixture was subjected to a separation by a centrifugation, to obtain a precipitate. The precipitate was washed in sequence with ultrapure water three times, and with ethyl alcohol three times, obtaining a washed precipitate. 0.2 g of the washed precipitate was dispersed into 60 mL of absolute ethyl alcohol again, and 64 mL of 2-methyl imidazole solution (with a concentration of 0.0625 g/mL) was added thereto, and they were uniformly mixed and sonicated for 5 min. 4 mL of cetyl trimethyl ammonium chloride (with a concentration of 5 wt %) solution was added therein, and they were stirred at room temperature for 5 min. 1.5 mL of tetraethoxysilane (TEOS) was slowly added dropwise therein, and they were stirred at room temperature for 1.5 h. The resulting mixture was centrifuged, obtaining a precipitate. The precipitate was washed with ultrapure water and ethyl alcohol three times each, obtaining $ZIF67@SiO_2$.

Figure 2:
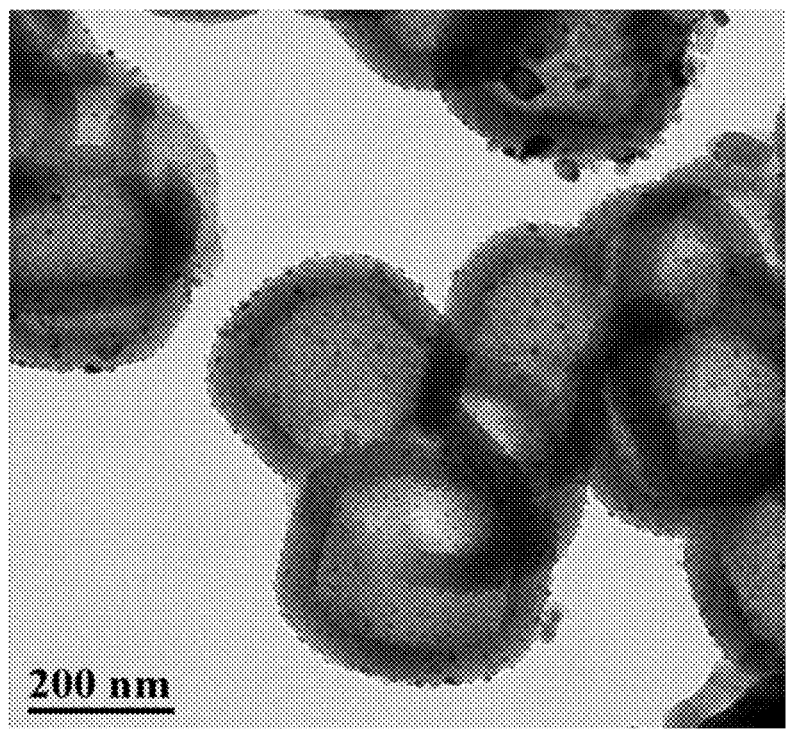
FIG. 2 shows a transmission electron micrograph of Co/C@SiO$_2$@Ni/C of Example 1 of the present disclosure.

0.1 g of $ZIF67@SiO_2$ was uniformly dispersed into 40 mL of ethyl alcohol aqueous solution (5:3) and sonicated for 10 min, and 5 mL of tris solution (with a concentration of 0.04 g/mL) was added into therein, they were mixed. Then 30 mg of dopamine and 75.2 mg of $NiCl_2 \cdot 6H_2O$ were added therein in sequence, and they were stirred at room temperature for 15 h after the dopamine and $NiCl_2 \cdot 6H_2O$ being dissolved completely. The resulting mixture was centrifuged (9000 rpm, 5 min), obtaining a precipitate. Finally, the precipitate was washed in sequence with ultrapure water three times, and with ethyl alcohol three times, obtaining a precipitate. The precipitate was placed in the oven and dried at 60° C. for 12 h, obtaining a precursor material. The precursor material was placed at the center of a quartz crucible and calcined at 500° C. for 12 h, with a heating rate of 2° $C. \cdot min^{-1}$, under the protection of nitrogen, obtaining black composite yolk-shell-structured nanomaterial $Co/C@SiO_2@Ni/C$. The scanning electron micrograph and transmission electron micrograph of $Co/C@SiO_2@Ni/C$ were shown in FIG. 1 and FIG. 2.

An affinity tag was introduced into the gene sequence that codes the organophosphorus degrading enzyme, to obtain a desired gene sequence. The desired gene sequence was transformed in a plasmid, and then the plasmid was transferred into a host *Escherichia coli*. The host *Escherichia coli* was subjected to fermentation. The cells in the fermentation broth were lyzed after the fermentation, and the resulting mixture was centrifuged, obtaining a crude enzyme solution of organophosphorus degrading enzyme labeled with the affinity tag.

A certain amount of composite yolk-shell-structured nanomaterial was added into a Tris-HCl buffer solution (50 mM, pH 8.0), and they were sonicated for 2 mM to be uniformly dispersed. The uniformly dispersed solution was added into a crude enzyme solution, and they were uniformly mixed, shook on a shaking table at room temperature for 3 h. The resulting mixture was subjected to a centrifugation, obtaining a precipitate. The precipitate was washed with imidazole buffer solution (40 mM) three times, obtaining a washed precipitate, i.e. the organophosphorus degrading enzyme based multifunctional catalyst OpdA@Co/Ni@Ni/C. The specific preparation example could refer to Table 1 below.

In order to verify the properties of organophosphorus degrading enzyme catalyst prepared by the present disclosure, to show its ability to degrade organophosphorus pesticide, the inventor used existing organophosphorus degrading enzyme as a comparative example which was purchased on the market. The purchased existing organophosphorus degrading enzyme was a commodity with a brand name of organophosphorus degrading enzyme biochemical detergent (Model PG-OPH-D1) from Tianjin Zhangda Science and Technology Development Co., Ltd, China, main component of which was organophosphorus degrading enzyme.

9 mg of the organophosphorus degrading enzyme based multifunctional catalysts prepared in Examples 1 to 4 and Comparative product were weighed respectively, and dispersed into 1.97 mL of Tris-HCl buffer solution (50 mM, pH 9.0), and 20 mg of $NaBH_4$ and 30 μL of parathion-methyl (10 mg/mL) were added thereto for reacting for 10 mM at 40° C., obtaining a reaction mixture. The reaction mixture was centrifuged, obtaining a liquid supernatant. 1 mL of the liquid supernatant was taken and mixed with 1 mL of phenol solution (5% (w/w)) and 1 mL of NaOH solution (0.5% (w/w)), obtaining a mixture. The mixture was subjected to a reaction in a water bath at 30° C. for 30 mM, obtaining a product, i.e. p-aminophenol. The content of p-aminophenol was measured at 630 nm with a spectrophotometer, and the test results were shown in Table 1.

TABLE 1

| Preparation Examples | support for immobilizing | Source of the organophosphorus degrading enzyme gene sequence | Affinity tag | Content of p-aminophenol |
|---|---|---|---|---|
| Example 1 | Composite yolk-shell-structured nanomaterial | Radioactive agrobacterium | Histidine tag | 0.57 μmol |
| Example 2 | Composite yolk-shell-structured nanomaterial | Flavobacterium | Histidine tag | 0.46 μmol |
| Example 3 | Composite yolk-shell-structured nanomaterial | Radioactive agrobacterium | tryptophan tag | 0.35 μmol |
| Example 4 | Composite yolk-shell-structured nanomaterial | Pseudomonas agrobacterium | cysteine tag | 0.32 μmol |
| Comparative Example | Existing organophosphorus degrading enzyme | | | 0.21 μmol |

Organophosphorus degrading enzymes could be used to catalyze the degradation of organophosphorus pesticides into p-nitrophenol. Compared with organophosphorus pesticides, p-nitrophenol is much less toxic, but it still has relative high toxicity and still causes pollution to the environment. In the presence of hydrogen donor, the composite yolk-shell-structured nanomaterial could be used to catalyze p-nitrophenol into p-aminophenol, which is a common pharmaceutical intermediate and has wide application value.

Therefore, it can be seen from the detection results in Table 1 that the organophosphorus degrading enzyme based multifunctional catalyst prepared by the method of the present disclosure has a better degradation effect for the organophosphorus pesticide, and exhibits a higher enzyme utilization rate, thereby having a better degradation effect, which is conducive to the application in the degradation of organophosphorus pesticides.

According to the present disclosure, the composite yolk-shell-structured nanomaterial could be used to purify and immobilize the organophosphorus degrading enzyme with an affinity tag to form the organophosphorus degrading enzyme based multifunctional catalyst. The prepared catalyst could be used to not only completely degrade organophosphorus pesticide, but also to detect organophosphorus pesticide.

Specifically speaking, a certain amount of the organophosphorus degrading enzyme based multifunctional catalyst was weighed, and mixed thoroughly with 5 μL of 10 mg/mL parathion-methyl (acetonitrile as solvent) and 995 μL of Tris-HCl buffer (50 mM, pH 8.0), and the resulting mixture was placed in a water bath at 37° C. and incubated for 5 min. Then, 1 mL of 10% trichloroacetic acid solution was added therein to terminate the incubating, and 1 mL of 10% $Na_2CO_3$ solution was added thereto for color development. The absorbance value was measured at OD410. Since p-nitrophenol exhibits a characteristic absorption peak at 410 nm and appears yellow in the presence of $Na_2CO_3$, the amount of the methylparathion pesticide could be judged by the color depth.

The above description is only a preferred embodiment of the present disclosure, and the present disclosure cannot be limited thereto, and any modifications, equivalent replacements and improvements made within the spirit and principle of the present disclosure, should fall within the scope of the present disclosure.

What is claimed is:

1. A method for preparing an organophosphorus degrading enzyme based multifunctional catalyst, comprising
directly adding a composite yolk-shell-structured nanomaterial into a crude enzyme solution of an organophosphorus degrading enzyme with an affinity tag, and mixing, to obtain a mixture, and subjecting the mixture to a separation, to obtain the organophosphorus degrading enzyme based multifunctional catalyst,
wherein the composite yolk-shell-structured nanomaterial is Co/C@SiO$_2$@Ni/C, and
the organophosphorus degrading enzyme is encoded by a gene sequence obtained from one of soil *pseudomonas, flavobacterium*, and radioactive *agrobacterium*.

2. The method of claim 1, wherein the affinity tag is selected from the group consisting of histidine tag, cysteine tag, and tryptophan tag.

3. The method of claim 1, wherein the mixing is performed by using a shaking table or stirring for 0.5-6 hours; and the separation is performed by centrifugation or filtration.

4. The method of claim 2, wherein the mixing is performed by using a shaking table or stirring for 0.5-6 hours; and the separation is performed by centrifugation or filtration.

* * * * *